United States Patent [19]
Dasgupta et al.

[11] Patent Number: 6,011,882
[45] Date of Patent: Jan. 4, 2000

[54] CHEMICAL SENSING TECHNIQUES EMPLOYING LIQUID-CORE OPTICAL FIBERS

[75] Inventors: Purnendu K. Dasgupta, Lubbock, Tex.; Su Yi Liu, Sarasota, Fla.

[73] Assignee: World Precision Instruments, Inc., Sarasota, Fla.

[21] Appl. No.: 08/951,254

[22] Filed: Oct. 16, 1997

[51] Int. Cl.[7] ........................................ G02B 6/00
[52] U.S. Cl. ...................... 385/12; 385/125; 250/227.18; 356/436
[58] Field of Search ................. 385/12.125; 250/227.14, 250/227.18, 459.1, 461.2, 473.1, 474.1; 356/301.133, 436

[56] References Cited

U.S. PATENT DOCUMENTS

| | | | |
|---|---|---|---|
| 3,679,312 | 7/1972 | Mansberg | 356/36 |
| 4,600,310 | 7/1986 | Cramp et al. | 356/432 |
| 4,867,919 | 9/1989 | Yafuso et al. | 264/1.5 |
| 5,444,807 | 8/1995 | Liu | 385/125 |

FOREIGN PATENT DOCUMENTS

WO 91/03730  3/1991  WIPO.

OTHER PUBLICATIONS

"Liquid-Core Waveguides for Chemical Sensing", Hong et al., SPIE vol. 2293, pp. 71–79, 1994.

*Primary Examiner*—John D. Lee
*Assistant Examiner*—Victoria D. Hao
*Attorney, Agent, or Firm*—Alix, Yale & Ristas, LLP

[57] ABSTRACT

A permeable optical fiber waveguide with a liquid core is employed as a probe for the detection or measurement of a chemical specie of interest by filling the waveguide core region with a light transmitting reagent liquid which undergoes a change in an optical characteristic thereof when exposed to the chemical specie and then inserting the filled waveguide into an environment in which the chemical specie may be present. The chemical specie, if present, will permeate through the waveguide wall and react with or be absorbed in the core liquid.

18 Claims, 2 Drawing Sheets

CHEMICAL SENSING TECHNIQUES EMPLOYING LIQUID-CORE OPTICAL FIBERS

BACKGROUND OF THE INVENTION

1. Field of the Invention

This invention relates to the optical detection of different chemical species and, particularly, to the identification and/or measurement of chemical substances of interest through detection of changes in the optical properties of a reagent/solvent caused by the reaction with or dissolution of the said chemical substance in the reagent/solvent. More specifically, the present invention is directed to optically detecting the presence, and/or concentration of species which are in the gas or vapor phase or are dissolved in a liquid matrix and, especially, to sensing changes in the optical properties of a confined light conducting medium resulting from exposure of the confining vessel to the sample matrix of interest. Accordingly, the general objects of the present invention are to provide novel and improved techniques of such character.

2. Description of the Prior Art

The use of fiber optics in chemical analysis is known in the art. In the prior art, there are two main classes of fiber optic based sensors employed in such analysis. In a first type of prior art sensor, a relatively long length of optical fiber is deployed as the sensing element and analysis light through the fiber interacts with the medium surrounding the fiber. This interaction occurs because the light used to internally illuminate the fiber, i.e., the analysis light, penetrates the external medium to a distance equivalent to ¼ of its wavelength, i.e., to a distance much less than the radius of the fiber. Such sensors are called evanescent wave sensors. The main disadvantage incident to the use of evanescent sensors is limited sensitivity. (See for example, "Fiber Optic Optrodes for Chemical Sensing", Brenci and Baldini, in Proceedings, 8th International Conference on Optical Fiber Sensors, pages 313–319, 1992; and "Fiber-Optic pH Sensor Based on Evanescent Wave Absorption Spectroscopy", Ge et al, Analytical Chemistry, volume 65, pages 2335–2338, 1993.)

In the second type of prior fiber optic based chemical sensor, which has found more practical applications when compared to the above-mentioned type device, light launched into the proximal end of an optical fiber emerges at the distal end thereof to interact with a "target" substrate or solution that is affected by the chemical composition of the medium in which the target is present. The light interaction can be probed by observing changes in either light absorption or the emission properties of the target substrate/solution. In a fluorometric mode of operation, a light beam of a wavelength suitable to excite fluorescence is launched through the fiber and the emitted fluorescent light is collected by, for example, the same fiber and separated by a suitable optical arrangement such as a dichroic mirror. (See, e.g., "Enzyme-based Fiber Optic Zinc Biosensor", Thompson and Jones, Analytical Chemistry, volume 65, pages 730–734, 1993); and "Fiber Optic pH Sensor Based on Phase Fluorescence Lifetime", Thompson and Lakowicz, Analytical Chemistry, volume 65, pages 853–856, 1993). Alternatively, the emitted fluorescent light can be collected by a second fiber(s). (See, e.g., "Novel Techniques and Materials for Fiber Optic Chemical Sensing", Wolfbeis, in Optical Fiber Sensors, Springer Proceedings in Physics, Volume 44, pages 416–424, 1989).

Absorptiometric measurements employing this second type of sensor typically implement a bifurcated collection technique, i.e., a second fiber(s) is used to receive the light to be analyzed. Most commonly, in absorption-type sensors, a reflecting optical target containing an immobilized reagent which undergoes a spectral change upon interaction with the analytes of interest in the surrounding medium is located at the fiber tip. Light (monochromatic or broadband) launched through the fiber is reflected off this target and single or multiwavelength measurements are made on the reflected light. (See, e.g., "Potentiometric and Fiber Optic Sensors for pH Based on an Electropolymerized Cobalt Porphyrin"), Blair et al, Analytical Chemistry, volume 65, pages 2155–2158, 1993; "Fiber Optic Sensors for pH and Carbon Dioxide Using a Self Referencing Dye", Parker et al, Analytical Chemistry, volume 65, pages 2329–2334, 1993; and "Current Developments in Optical Biochemical Sensors", Narayanaswamy, Biosensors and Bioelectronics, Volume 6, pages 467–475, 1991). Such immobilized reagents can also be used for fluorescence measurements. (See, e.g.,"Fluorocarbon-based Immobilization of a Fluor-oionophore for Preparation of Fiber Optic Sensors", Blair et al, Analytical Chemistry, volume 65, pages 945–947.)

The employment of an immobilized reagent, while attractive in theory, generally results in a sensor with a limited lifetime due to reagent loss from photodecomposition or leaching. To solve this problem, resort has been had to renewing the reagent and, particularly, to flowing the reagent the sensor probe. (See, e.g., "Measurement of Seawater $pCO_2$ Using a Renewable-Reagent Fiber Optic Sensor with Colorimetric Detection", DeGrandpre, Analytical Chemistry, volume 65, pages 331–337, 1993). In the extant art embodying such flow-through sensors, the tip of the optical fiber is typically located at a first end of a cylindrical chamber, and a reflector is disposed at the opposite end of the chamber. Provision is made for the continuous introduction of a suitable reagent and its withdrawal via conduits which are in fluid communication with the chamber and, typically, oriented in parallel with the optical fiber. The chamber will in part be permeable to the analyte of interest. The analyte thus permeates through a chamber wall and reacts with the reagent thereby producing a change that can be optically monitored. The rate of reagent flow governs the attainable sensitivity, i.e., sensitivity increases with decreasing flow, and response time, i.e., response time decreases with increasing flow. In the reflectance mode, as described above, the effective path length is twice the distance between the fiber tip and the oppositely disposed reflector. The sensor can also be configured with a transmitting fiber at one end of the chamber and an oppositely disposed receiving fiber whereby the path length essentially becomes the length of the chamber. In either case, limited pathlengths are generally attainable, due to severe light loss, and maximum achievable sensitivity is very limited.

Collection of analytes into a reagent flowing through a permeable membrane is well known in the art. The collected analyte is typically measured colorimetrically or fluorometrically in a system external and separate from the collector with or without further reagent addition and reaction. If a sufficient membrane area is provided for analyte collection, parts per trillion levels of analytes can be detected in favorable cases. (See, e.g., "Determination of Gaseous Hydrogen Peroxide at Parts per Trillion Levels with a Nafion membrane Diffusion Scrubber and a Single-Line Flow-Injection System", Dasgupta et al, Analytica Chimica Acta, Volume 260, pages 57–64, 1992; and "Measurement of Atmospheric Ammonia", Dasgupta et al, Environmental Science and Technology, Volume 23, pages 1467–1474, 1989). The sensitivity of a renewable-reagent fiber optic sensor employing this mode of analyte collection would be expected by those skilled in the art to be very low because the length of the membrane that can be used is constrained by the light loss through the membrane.

A renewable reagent liquid core waveguide chemical sensor which uses a membrane material as both the sampling and waveguiding component has been reported. (See, e.g., "Liquid Core Waveguides for Chemical Sensing", Hong and Burgess, Proceedings SPIE, Vol. 2293, pgs. 71–79, 1994). This paper proposes a liquid core waveguide comprised of then available permeable polymers, i.e., PTFE and FEP. Such waveguides, however, have very limited utility because their refractive indexes are greater than that of water, i.e., exceed 1.33, and because they are not optically clear and thus can conduct light for only a short distance. Further, while permeable to gases, such polymers do not have sufficient permeability to function as a sensor probe with significant commercial applicability. In the use of such waveguides, it is necessary to incorporate ethylene glycol or some other non-aqueous solvent(s) in the liquid core, to raise the refractive index of the core above that of the containment tube, and this further limits utility.

The paper discussed immediately above also discussed the use of Teflon A.F. as an internal coating on a porous polyethylene hollow support fiber, the thickness of the coating being on the order of 1 $\mu$m. The resulting tube was filled with an acid-base indicator and reportedly responded to relatively high concentrations of ammonia gas (statically deployed in the vapor space over a 0.01 M solution of ammonia in a 50 mL capacity closed vessel) with a seemingly rapid response time (ca. 1 min). Coating the inside of a thin-walled porous fiber with the "AF" solution to produce an ultrathin layer of the latter polymer to produce a reliable or reproducible waveguide is not a commercially practical solution because, as is well known, "Teflon", including the AF variety, has very poor surface adhesion to most material unless special adhesion promoters are used (see, e.g., P. Dress and H. Franke, "A Cylindrical Liquid-Core Waveguide", Applied Physics, Part B, Volume 63, pages 12–19, 1996); and because such surface promoters can compromise the structural integrity of the porous tubing used as support. Also, it is impossible to produce uniform thicknesses of a polymer coating in the manner reported over any reasonable length of a tube and, especially, to produce such a coating in a reproducible manner from one batch to another. Further, it would be impractical to produce such thin coatings on a practical basis without periodic occurrence of pinholes and this would make it impossible to use such tubing in in-vivo physiological applications or in any situation involving significant external pressure, e.g., for a situation in which a sensor is to be immersed in the depths of the ocean. In the latter case, the high collapsibility of supporting porous membrane tubes when pressure is applied from the outside will also compromise the structural integrity of such a sensor.

Importantly, the data provided by Hong and Burgess for the response speed of their "Teflon AF" coated tube teaches away from the use of a polymeric tube solely composed of "Teflon AF", rather than a bilayer structure involving a porous support structure and a "Teflon AF" adlayer. This is because the response time in the Hong-Burgess design is solely due to the permeation through the 1 $\mu$m thick "Teflon AF" layer, i.e, the transport in the support structure occurs through the free pore space in a microsecond time scale (the characteristic diffusion time of ammonia a gas with a diffusion coefficient of 0.25 cm$^2$/s through a 55 $\mu$m deep (see Hong and Burgess, page 78) air-filled pore is only 120 msec.

The ~1 min response time for this device for a 1 $\mu$m thick layer as seen in FIG. 9 of Hong and Burgess is actually not fast but very slow, when the thickness is taken into account. It is well known that the characteristic time (loosely, response time for transport) for diffusive or permeative transport across a polymer wall varies directly with the square of the thickness of the polymer wall and inversely as the diffusion coefficient of the analyte of interest through the polymer. For a given analyte and polymer the diffusion coefficient remains constant and thus the response time increases with the square of the thickness (see, e.g., Dasgupta, P. K., "A Diffusion Scrubber for the Collection of Atmospheric Gases", Atmospheric Environment, Volume 18, pages 1593–1599, 1984). Hong and Burgess's own data on PTFE membranes (page 78) show the same behavior. The response time for ammonia decreases by a factor of ~4 as the membrane thickness is reduced by a factor of two (from 150 to 84 $\mu$m). Accordingly, if a polymer of ~1 $\mu$m thickness produces a response time ~1 min (and this for ammonia, a relatively low molecular weight, small, fast diffusing molecule), the response time for a 75 $\mu$m thick tube would be expected to be 5,625 minutes or close to 4 days, if one were to follow the teachings of Hong and Burgess. A "Teflon AF" tube having a wall thickness significantly less than 75 $\mu$m would not have sufficient rigidity to be employed as a sensor probe.

SUMMARY OF THE INVENTION

The present invention overcomes the above-briefly discussed and other deficiencies and disadvantages of the prior art by providing novel and improved optical analyses techniques. The present invention thus encompasses a new and novel method by which chemical substances of interest may be detected and/or measured using optical means. The invention exploits two properties unique to a special kind of polymer membrane which has the following important properties: 1) the membrane structure is permeable to gases, vapors and certain chemical substances dissolved in a liquid matrix, 2) the membrane is comprised of a polymer material which is amorphous, optically clear and has a refractive index which is less than 1.33, and 3) the membrane can be formed into various self-supporting cylindrical shapes which, when filled with liquid, comprise an optical waveguide. The inside of the waveguide will be filled with a light conducting liquid. Also, any of a wide range of well known chemical solutions whose optical properties are modified when exposed to permeant gases or vapors can be dissolved in the waveguide filling fluid. In the practice of the invention to sense and measure chemical substances of interest, the exterior surface of the permeable waveguide is exposed to an environment in which the substances may be present in the gas or vapor phase of may be dissolved or dispersed in a liquid. Light is "shown" by various means in the interior of the polymer waveguide. The light leaving the waveguide is then "measured". Light measuring techniques such as optical absorption (colorimetry), luminescence, fluorescence and Raman spectra can be used as modalities with which to characterize the substances to be detected and measured.

The invention thus employs a unique permeable liquid core waveguide wherein an appropriate light transmitting reagent forms the waveguide core. This permeable waveguide is fabricated from an optically clear amorphous polymer material having a lower refractive index than the flowing or stationary light transmitting reagent core liquid. A preferred material for use as the containment tube of a reagent core waveguide for practice of the invention is the copolymer of 2,2'-bis-trifluoromethyl-4,5 difluoro-1,3 dioxole (PDD) with tetrafluoroethylene (TFE) (TEFLON AF 2400). The reagent core liquid inside the waveguide is itself or contains a chemical indicator that will change its optical characteristics when the waveguide sensor is exposed to the analyte, the analyte diffusing through the highly permeable tube wall(s). The optical changes may, in accordance with the invention, be detected by one of the following techniques: UV/Vis absorption, fluorescence, chemiluminescence, or Raman spectrometry.

The design flexibility of a combined liquid core optical waveguide/gas or vapor sensor as described above for use in the practice of the invention allows a broad spectrum of uses, i.e., the sensor may be embodied in a probe having a length of a few millimeters to a few meters depending on the application and the sensitivity requirements. A short length waveguide is particularly well suited for applications that require a small sensor such as, for example, in-vivo biological sensors. The longer waveguide lengths will permit greater sensitivity or faster response times and may be particularly useful in environmental measurements.

BRIEF DESCRIPTION OF THE DRAWINGS

The ability of those skilled in the art to understand the present invention, and to appreciate its numerous advantages, will be enhanced by reference to the accompanying figures in which.

DESCRIPTION OF PREFERRED EMBODIMENTS

Figure 1:
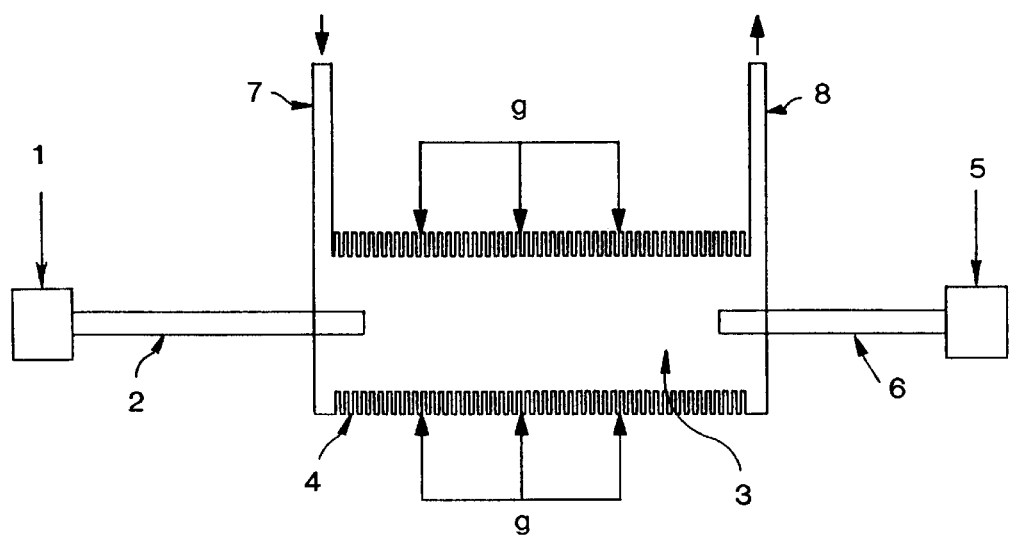
FIG. 1 is a schematic illustration of a first embodiment of a flow-through sensor for use in the practice of the invention.

The present invention employs a liquid core waveguide as the main body, i.e., the probe, of a sensor. Referring to FIG. 1, the liquid core waveguide, indicated generally at 4, includes a substantially optically transparent liquid core region 3 surrounded by a material, i.e., tube 4, having a lower refractive index (relevant to the wavelength range of light used) than the liquid material comprising the core. Light will propagate inside the waveguide with negligible losses due to the total internal reflection at the surface of the lower refractive index material provided that the launching angle of the light into the core is within the acceptance angle of the material comprising tube 4.

In practice of the invention, the sensor probe of FIG. 1 is coupled to a light source 1 which illuminates the core liquid 3 via a solid optical fiber 2, or bundle of such fibers, indicated generally at 2. Light exits the waveguide at the end opposite to fiber 2 and is collected by an optical fiber(s) 6. Optical fiber(s) 6 deliver the collected light to an analysis instrument 5. FIG. 1 illustrates a "flow-through" technique wherein the core liquid 3, i.e., the indicator reagent, is delivered to the core region of the waveguide sensor via a supply conduit 7 and exits the core region via a discharge conduit 8. In a stationary, i.e., non-flowing, reagent embodiment, one of conduits 7 or 8 would be used to fill the core region of the waveguide with the reagent, after which the conduit would be capped, and the other conduit would be omitted.

The wall material of tube 4 must meet certain basic requirements. Firstly, it has to be permeable to the analyte and it must have a refractive index that is lower than that of the reagent, i.e., the core liquid 3. Secondly, it must be optically clear. Thirdly, it must be relatively rigid so that, if the use dictates, the probe will be self-supporting. A preferred waveguide defining material is TEFLON AF 2400 which is the copolymer of PDD with TFE. It has recently been learned how to extrude PDD-TFE in the form of tubing having a wall thickness of 75 $\mu$m.

The tubing 4 has several important functions. Firstly, it forms a total reflection layer to entrap light injected via fiber 2 inside the tube 4 so as to form a light waveguide. To form a liquid-core light waveguide, the tubing must define an outer layer with a refractive index which is lower than that of the liquid core. Since the copolymers of PDD with TFE have a refractive index in the range of 1.29 to 1.31, i.e., a refractive index which is lower than water and most organic solvents, almost any liquid can be used as the core liquid in a TEFLON AF 2400 tube. The waveguide action will significantly increase the signal-to-noise ratio of the analysis technique when compared to the prior art. This increase in sensitivity, in turn, allows the choice of a detection mode that will reduce the cost of detection. When UV/Vis absorption spectroscopy is used as the detection method, the waveguide action of the reagent-filled part of the sensor helps maintain high light throughput to the receiving fiber 6, making possible a long length and a large surface area for influx of the analyte, in the manner to be described below, into the sensor. In the absence of large light losses, the signal-to-noise ratio is linearly related to the amount of analyte transported into the sensor. In the prior art, the light pathlength of the sensor has typically been only 1 mm long because of the inherent difficulty in keeping the light throughput for a longer path. In the practice of the present invention, a one meter long waveguide can be easily used, resulting in a signal-to-noise ratio improvement of three orders of magnitude over a sensor with 1-mm length, with a proportionate improvement in the limit of detection. When fluorescence, Raman, or chemiluminescence spectroscopy is used as the detection technique in instrument 5, the waveguide will enhance the signal by the integrating light signal, i.e., the additive effect which occurs along the waveguide. As will be obvious to those skilled in the art, when chemiluminescence is the detection modality, light injection via fiber 2 is not required.

The tubing 4 must also reduce interference caused by the effects of ambient light on the sensor. This result is accomplished because the optically clear, low refractive index tubing wall not only functions as a total reflection layer to keep the transmitted analysis light inside the waveguide, but it also substantially prevents ambient light from propagating through the lumen of the waveguide. Restated, any ambient light that is within the acceptance angle of the receiving fiber 6 will also be within the "total rejection angle" of the tubing 4. Therefore, although the tubing behaves like a mirror to internal light, it appears transparent to ambient light. Accordingly, ambient light is "rejected" while the internal guidance of analysis light and/or internally generated light is enhanced. A further reason of the relative immunity of the liquid-core guide sensor of the invention to the deleterious effects of ambient light is its high throughput of internal light which makes penetration of a fixed amount of ambient light less important.

The thin walled tube 4 must additionally function as an efficient analyte permeable membrane. Not only does the PDD-TFE copolymer display the lowest refractive index of any polymer, whereby it may function as a liquid core waveguide when filled with almost any clear liquid, it is also much more gas permeable than other fluoropolymers. Published data indicate that TEFLON AF 2400, for example, is 230 times more permeable to $CO_2$, $O_2$ and $H_2$ than polytetrafluoroethylene (PTFE). In the case of $CO_2$, the permeability of TEFLON AF 2400 to $CO_2$ is 3900 Barrer. Indeed, the permeability of PDD-TFE copolymers is comparable to that of polydimethylsiloxane (see, e.g., "Gas and Vapor Transport Properties of Amorphous Perfluorinated Copolymer Membranes Based on 2,2-bis trifluoromethyl-4,5-difluoro-1,3-dioxole/tetrafluoroethylene", Pinnau and Toy, Journal of Membrane Science, Volume 109, pages 125–133, 1996). In FIG. 1, the migration of gas or vapor from the ambient environment to the core liquid through the permeable wall of tube 4 is indicated by "g".

The PDD-TFE tubing 4 also has sufficient rigidity to provide mechanical support for the associated components of the sensor. The analyte flux into the sensor is not only linearly dependent on available membrane area, it is also dependent inversely on the thickness of the membrane. Most gas permeable membrane tubes, because they have to be very thin to obtain sufficient flux, are lacking in rigidity and cannot be used as the structural support of the sensor. Thus, for a waveguide of any significant length, additional means of mechanical support would normally be necessary. The PDD-TFE copolymer displays high mechanical strength and rigidity. A narrow bore tube 4 with 75 μm thick walls is strong enough for most biological applications.

As noted above, the wall of polymeric tubing 4 provides containment for the reagent/core liquid 3. Transport of the analyte through the tube wall, as noted, occurs by permeation. The process of permeation is governed by a combination of solubility in the polymer and diffusion through the polymer. For ionic constituents in a solution or other high molecular weight substances, the vapor pressure is very low and there is negligible loss of the internal constituents through the sensor wall.

The present invention can be practiced in several modes. For example, the reagent inside the waveguide can be used in either a flowing or stationary manner. For a stable reagent that can be used in an equilibrium fashion, for example when sensing $pCO_2$ using a carbonate-bicarbonate buffer with an additional pH indicator, or when the sensor is to be disposable or where long term usability is not an important consideration, the indicator reagent can be permanently sealed inside the waveguide. Such non-flowing sensors will be stored inside a sealed package to prevent contamination of the reagent inside the waveguide from ambient air between fabrication and use. Where a stationary reagent core is used, the FIG. 1 sensor may be modified to permit the indicator reagent to be replaced or refurbished by including sealable liquid in/out caps, through which the waveguide can be filled with a fresh reagent, on one or both of conduits 7 and 8. For indicators that are chemically or photolytically unstable, the reagent will be continuously refreshed by using the waveguide essentially as a flow cell as represented by FIG. 1. For many applications, the optimum mode may be the use of a stationary liquid core for a desired measurement period, to cumulatively build the maximum analyte concentration possible, followed by flushing and recharging the core at the end of that measurement period to ready the sensor for a new measurement.

In yet another embodiment, the liquid core waveguide can be used in combination with another membrane that collects the analyte, followed by one or more sequential reagent additions and reactions. Those skilled in the art will perceive that plural analyte collection step could be sequentially carried out with the liquid core of the waveguide of FIG. 1 forming the final reaction zone.

A further mode of practice of the invention is to employ a solvent in which the gas specie of interest will dissolve in the core liquid of the permeable waveguide. Since the liquid core waveguide is a very sensitive detector, many permeated analytes can be detected directly by the spectral signature characteristic of the analyte gas itself, dissolved in a suitable liquid, without any reaction with an indicator reagent. For example, most of the volatile organic compounds have a strong absorbance band in the UV range. With a one meter long flow cell, such compounds can be detected at a concentration of 10 nanomolar. With the use of Raman spectroscopy as the detection mode, it is possible to differentiate between a variety of analytes and simultaneously measure them, although there will be some sacrifice in sensitivity relative to UV/Vis absorbance detection.

Figure 2:
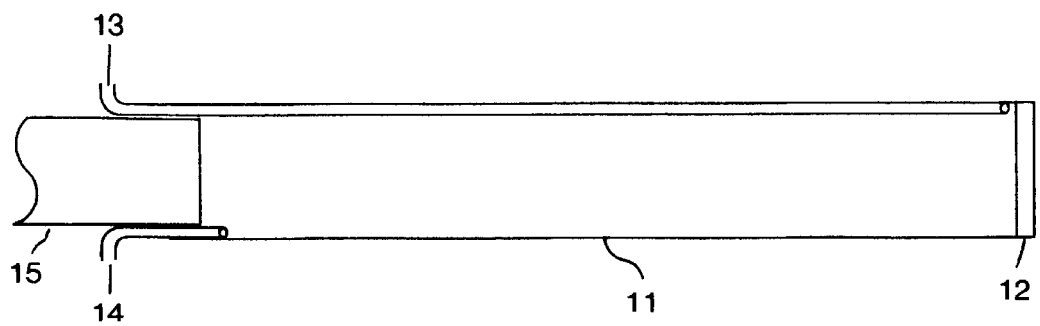
FIG. 2 is a schematic showing of a modified version of sensor of FIG. 1.

FIG. 2 depicts another sensor probe for use in practice of the invention. The sensor of FIG. 2 employs a gas and vapor permeable tube 11 as a liquid core optical waveguide. A suitable reagent is delivered into tube 11 via a conduit 13 which is arranged to have its discharge end located adjacent the distal end of waveguide 11. When the FIG. 2 sensor is operated in the flow-through mode, the reagent will exit waveguide 11 via a discharge conduit 14. Analysis light is launched into the proximal end of the waveguide core region via an optical fiber(s) 15. Light transmitted down the waveguide core is reflected at the distal end thereof by a mirror 12 and fiber(s) 15 thus functions as both the analysis light launching and collection modality. The manner in which this is accomplished may, for example, be as explained in the description of FIG. 2 of U.S. Pat. No. 5,444,807. Obviously, the pathlength for the light in the sensor of FIG. 2 is essentially twice the length of tube 11.

Figure 3:
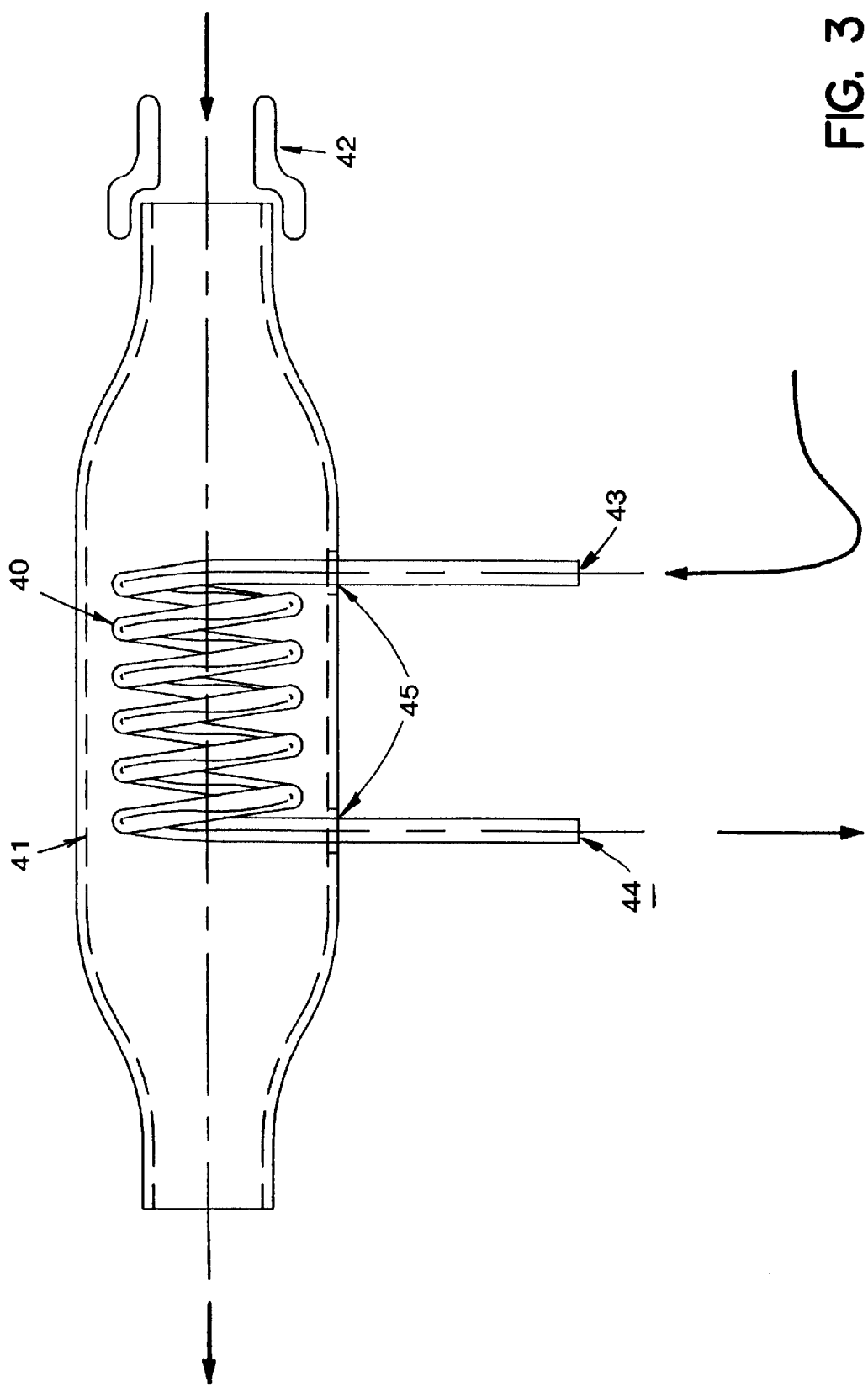
FIG. 3 schematically shows the practice of a sensing technique in accordance with the invention.

FIG. 3 exemplifies a special application of the present invention. In FIG. 3, the sensor comprises a helical coil of permeable polymer tubing 40 mounted in a larger cylindrical housing 41 having a mouthpiece 42 at one end. A human subject will respire through the mouthpiece. His/her respiratory gases pass over the helical coil structure and exit via the opposite open end of housing 41. The helical coiled shape of tubing 40 assures that a large length of the liquid reagent core waveguide formed thereby will be exposed to respired gases within the relatively small volume of the breath-through housing 41. The surface area of the permeable waveguide within the containment cylinder is thus maximized and, accordingly, the sensitivity of the probe that will be exposed to the transient gases of interest is also maximized. The ends of the helical coil exit the housing 41 via small holes 45 which are sealed with an appropriate adhesive. Excitation light and core fluid are delivered to the proximal end 43 of the helical coil 40. The exit point for both the core fluid and the attenuated light signal is indicated at 44.

The following are illustrative examples of practice of the present invention. $CO_2$ Detection: $CO_2$ may be sensed by filling the waveguide with an aqueous carbonate-bicarbonate buffer solution containing a pH indicator that undergoes a spectral change around the pH of such a buffer solution. Suitable pH indicators are phenol red and bromthymol blue. Visible absorption spectroscopy is used for sensing. The concentration of $CO_2$ outside the sensor (whether it is dissolved $CO_2$ in water or ambient $CO_2$ in the gas phase) quickly reaches equilibrium with $pCO_2$ (partial pressure of $CO_2$) inside the sensor. The pH inside the sensor and hence the exact spectrum of the indicator depends on the $pCO_2$ level. All general considerations relevant to any other fiber optic based $CO_2$ sensors will apply (see, e.g., DeGrandpre, above).

$O_2$ Detection: Oxygen may be sensed through utilization of both fluorometric and absorptiometric principles. Many fluorescent aromatic dye stuffs are known that are fluorescent and their fluorescence markedly decreases in the presence of oxygen due to Stern-Volmer Quenching. $O_2$ can be sensed using a solution of an oxygen-quenchable fluorescent dye inside the liquid waveguide. Inexpensive and highly sensitive absorptiometric oxygen sensing can be accomplished by filling the liquid core waveguide with a solution/suspension of leuco-methylene blue. This colorless dye substrate is readily-oxidized by oxygen to form methylene blue which can be monitored by the emission from a red light emitting diode (LED). Other reagents such as ammoniacal cuprous chloride or chromous chloride (Chromium (II) chloride) which readily absorb oxygen to form highly colored products can also be used in the absorptiometric mode.

CO Detection: It is known that an alkaline solution of silver p-sulfoaminobenzoate or a solution of potassium tetrachloropaladate(II) readily absorbs CO and respectively form silver or palladium in a colloidal form that can be monitored by optical absorption measurement around 400 nm. Such solutions can be readily used for making a liquid core waveguide sensor for CO.

$H_2S$ Detection: Hydrogen sulfide is readily absorbed by an alkaline solution of sodium nitroprusside to from an intense purple color that can be monitored by emission from a green or yellow light emitting diode (LED) (see, e.g., "Nitroprusside and Methylene Blue Methods for Silicone Membrane Differentiated Flow-Injection Determination of Sulfide in Water and Wastewater", Kuban et al, Analytical Chemistry, Volume 64, pages 36–43, 1992). This can form the basis of a highly sensitive and selective method for the measurement of $H_2S$ in ambient air and wastewater with an LED and a liquid core waveguide.

$NO_2$ Detection: Nitrogen Dioxide forms an intensely purple dye that can be monitored with a green LED upon reaction with Griess-Saltzman reagent (sulfanilic acid or sulfanilamide with 1-naphthylethylenediamine hydrochloride in a dilute acetic acid medium). Accordingly, by filling a liquid core waveguide with this reagent, $NO_2$ and/or nitrous acid may be selectively sensed. $NO_2$ can also be sensed in the lumionometric mode when a solution of luminol and sulfite is used in the waveguide, this reaction selectively producing chemiluminescence with luminol.

$NH_3$ Detection: High levels of ammonia can be monitored, employing the above-described principles of the $CO_2$ sensor, using an $NH_3$—$NH_4Cl$ buffer solution and an appropriate pH indicator and visible absorbance detection. Much lower levels of ammonia can be monitored using a system in which the ammonia is captured in a phenol-sodium nitroprusside solution followed by two sequential reactions, i.e., (a) with alkaline EDTA and then (b) with sodium hypochlorite. (see, e.g., "Electroosmotically Pumped Capillary Format Sequential Injection Analysis with a Membrane Sampling Interface for Gaseous Analytes", Liu and Dasgupta, Analytica Chimica Acta, Volume 308, pages 281–285, 1995). The color of the indophenol blue formed can be monitored with an orange-red LED emitting at 630 nm. An even more sensitive method consists also of a sequential reaction system and fluorometric sensing. In the latter technique, the ammonia is collected into an acidic receptor liquid and reacts with separately introduced solutions of o-phthalaldehyde and 2-mercaptoethanol (or sulfite) to form an intensely fluorescent isoindole.

Ozone Detection: Ozone can be detected either in the luminometric or the absorptiometric mode using the liquid-core waveguide. A great variety of intensely fluorescent dyes, including Eosin or Rhodamine, are oxidized by ozone and the oxidation is accompanied by light emission. Ozone also selectively decolorizes indigo derivatives and this bleaching can be monitored with a LED-based detector (see, e.g., "Automated Measurement of Aqueous Ozone Concentration", Darby et al, Process Control and Quality, volume 6, pages 229–243, 1995). Either sensing mode can be used for the monitoring of ozone in ambient air or for process control applications in ozonation plants for the production of potable water.

Hydrogen Peroxide Detection: Measurement of hydrogen peroxide has become important because it is the sterilizing agent of choice in many bioreactor operations. Hydrogen perioxide can be determined luminometrically using alkaline luminol containing a catalyst such as potassium ferricyanide in the core of the waveguide, this reagent produces intense chemiluminescence when contacted with $H_2O_2$. Hydrogen peroxide can also be monitored fluorometrically by using an oxidizable phenolic substrate such as p-Cresol and a peroxidase enzyme or its suitable mimic such as an ammoniacal solution of bovine hematin in the core of the waveguide. The resulting product is intensely fluorescent. Many calorimetric methods for measuring $H_2O_2$ are also known in the art.

Chlorine Detection: Chlorine is routinely monitored in water and air environments both in industry and by consumers. Chlorine reacts selectively with o-tolidine or tetramethylbenzidine in solution to form intensely yellow products that can be monitored by filling such a solution inside a liquid core waveguide and using a blue LED as the source for absorptiometric measurements.

Concentrated Acid Detection: The measurement of concentrated acids is an important problem in many industries. In the nuclear material processing industry, concentrated $HNO_3$ and HCl solutions are frequently used and it is important to measure the acidity in such media. This cannot be accomplished with simple pH sensing. Renewable reagent fiber optic based sensors have been used to address the problem using ion permeable membranes but there are difficulties due to the permeability dependence of such membranes on the presence of other membranes (see e.g., "A Renewable-Reagent Fiber-Optic Sensor for Measurement of High Acidities", Kuhn and Dyke, Analytical Chemistry, Volume 68, pages 2890–2894, 1996). Molecular $HNO_3$ and HCl can permeate through PDD-TFE and thus the use of a liquid core waveguide with a buffered indicator solution inside offers an ideal solution to this problem.

Detection of Organic Compounds in Water: The foregoing examples have served to show that the analytes that can be detected/identified through practice of the present invention can be in the gas phase or the solution phase. The only criterion that determines the applicability of the invention is sufficient permeability of the target analyte through the waveguide defining membrane. Thus, the invention has applicability to the determination of dissolved organics in water whether these are present in trace amounts or in larger concentrations as occur in leakage of organic solvents or fuel from underground storage/disposal facilities into groundwater. In many cases, it will be possible to provide an organic solvent that is transparent in the near infrared (NIR) spectroscopy range or substantially into the UV range as the core of the waveguide which will collect the contaminants from water and on which direct NIR or UV spectroscopy can be carried out. In a second mode, specific reactions can be carried out with many organic compounds to yield products that are easily optically detectable. Intensely colored products are formed from halocarbons (contamination of ground water for example by chlorinated hydrocarbons is of considerable concern) by the Fuliwara reaction. A reaction based fiber optic sensor has already been reported for this purpose (see, e.g., "Multicomponent Determination of Chlorinated Hydrocarbons Using a Reaction-Based Chemical Sensor. 1. Multivariate Calibration of Fujiwara Reaction Products", Henshaw et al, Analytical Chemistry, Volume 66, pages 3328–3334, 1994). The same reaction approach can be directly adapted to the present liquid core waveguide sensor with far greater sensitivity.

In the above discussion, it is implicit that laser and other light sources such as tungsten lamps, LEDs, mercury arc and others will be used as light sources for fluorescence and absorption measurement of the indicator fluid. A laser light source can be used in the present invention as means to generate Raman light spectra. Raman spectra have the particular advantage that molecules in the indicator fluid can exhibit unique "signature" spectra; thus enabling the separate analysis of specific molecules within a multi-molecular mixture in the fluid. The unique benefits of Raman spectroscopy within a liquid filled waveguide have been described in U.S. Pat. No. 5,604,587. Thus, when Raman spectroscopy is used as the analysis modality, the spectrum of chemicals that can be measured employing the present invention can be significantly broadened vis-a-vis the prior art. Raman spectroscopy with fiber optical sensors have not previously found practical applications due to limited sensitivity. In the practice of the present invention, a Raman signal which is enhanced at least more than 100 times when compared to the prior art may be achieved when a meter long waveguide is used.

While preferred embodiments have been described, various modifications and substitutions may be made thereto without departing from the spirit and scope of the invention. Accordingly, it is to be understood that the present invention has been described by way of illustration and not limitation.

What is claimed is:

1. A method for optical detection of chemical substances comprising:

forming a tubular self supporting member, said tubular member defining a hollow axial core region, said tubular member consisting essentially of an optically clear material which is gas and vapor permeable and liquid impervious, said material having a refractive index which is less than 1.33;

filling the core region of the tubular member with a light transmitting liquid reagent having an index of refraction which exceeds that of said material comprising said tubular member whereby said tubular member may function as a liquid core optical waveguide, said liquid undergoing a change in an optical characteristic thereof upon exposure to a chemical substance of interest which has diffused through said tubular member;

passing light through the liquid reagent;

receiving light which has passed through the liquid reagent; and detecting a change in an optical characteristic of the liquid reagent by analyzing the received light.

2. The method of claim 1 wherein the step of passing comprises:

injecting analysis light into the core region of the tubular member at an end thereof, the injected light being guided by the tubular member whereby the analysis light travels through the liquid reagent.

3. The method of claim 2 wherein the step of detecting comprises sensing analysis light which is not absorbed by passage through the liquid reagent in the core region of the tubular member.

4. The method of claim 2 wherein the step of passing comprises directly coupling an optical fiber to the core region and launching analysis light into the core region with a launching angle that is within the acceptance angle of the liquid core waveguide.

5. The method of claim 1 wherein the step of detecting comprises sensing fluorescence of said reagent.

6. The method of claim 5 wherein the step of passing comprises launching excitation light into the core region with a launching angle that is outside an acceptance angle of the liquid core waveguide.

7. The method of claim 1 wherein the step of detecting at least in part comprises sensing luminescence of said reagent.

8. The method of claim 1 wherein said tubular member is a single layer.

9. The method of claim 8 wherein said tubular member is non-porous.

10. The method of claim 8 wherein said tubular member includes a wall having a thickness of about 75 micrometers.

11. The method of claim 1 wherein said tubular member consists of a PDD-TFE copolymer.

12. A method for optical detection of a chemical substance comprising the steps of:

selecting a self-supporting tubular member comprised of a single layer of optically clear amorphous polymer having a refractive index of less than 1.33, the polymer being impermeable to a liquid delivered to the core region thereof and being permeable to gas and vapor, the tubular member being capable of functioning as an optical waveguide when the core region thereof is filled with a light conducting liquid having an index of refraction which exceeds 1.33;

filling the core region of the tubular member with a liquid which undergoes a change in an optical characteristic thereof upon exposure to a chemical substance of interest, said liquid having an index of refraction which exceeds that of the tubular member, the filled tubular member thereby defining an optical waveguide;

exposing at least a portion of the exterior of the filled tubular member to an ambient environment which may include the chemical substance of interest; and monitoring changes in an optical characteristic of the liquid which occur upon permeation of the chemical substance of interest from the ambient environment through a wall of the tubular member.

13. The method of claim 12 further comprising:

transmitting analysis light into the liquid confined within the core region of the tubular member with a launching angle which is within the acceptance angle of the liquid core optical waveguide comprising the filled tubular member.

14. The method of claim 13 wherein the step of monitoring comprises:

measuring the absorption of the transmitted analysis light by the liquid in the waveguide core region.

15. The method of claim 13 wherein the step of monitoring comprises:

measuring the fluorescence which occurs in the liquid in the waveguide core region.

16. The method of claim 12 wherein the step of monitoring comprises:

measuring the luminescence of the liquid in the waveguide core region.

17. The method of claim 12 wherein the step of monitoring comprises:

measuring the Raman spectra of the liquid in the core region of the waveguide.

18. The method of claim 12 wherein said tubular member includes a wall having a thickness of about 75 micrometers.

\* \* \* \* \*